US007348569B2

(12) United States Patent
Feurer et al.

(10) Patent No.: US 7,348,569 B2
(45) Date of Patent: Mar. 25, 2008

(54) ACCELERATION OF CHARGED PARTICLES USING SPATIALLY AND TEMPORALLY SHAPED ELECTROMAGNETIC RADIATION

(75) Inventors: Thomas Feurer, Bern (CH); Darius H. Torchinsky, Boston, MA (US); Keith A. Nelson, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 357 days.

(21) Appl. No.: 11/155,011

(22) Filed: Jun. 16, 2005

(65) Prior Publication Data

US 2005/0279947 A1 Dec. 22, 2005

Related U.S. Application Data

(60) Provisional application No. 60/581,194, filed on Jun. 18, 2004.

(51) Int. Cl.
*G01K 1/08* (2006.01)
*H01J 3/14* (2006.01)
*H01J 3/26* (2006.01)

(52) U.S. Cl. .................. 250/400; 315/5.41; 315/4; 315/5; 315/5.42; 315/3; 315/382.1; 372/2; 328/233

(58) Field of Classification Search ............ 250/400; 315/3, 4, 5, 5.41, 5.42, 382.1; 372/2; 328/233
See application file for complete search history.

(56) References Cited

U.S. PATENT DOCUMENTS

| | | | | |
|---|---|---|---|---|
| 4,570,103 A | * | 2/1986 | Schoen | 315/5.41 |
| 5,682,262 A | * | 10/1997 | Wefers et al. | 359/305 |
| 5,719,650 A | | 2/1998 | Wefers et al. | |
| 2002/0106046 A1 | * | 8/2002 | Fujimoto et al. | 376/156 |
| 2003/0038603 A1 | * | 2/2003 | Mako et al. | 315/382.1 |
| 2005/0167610 A1 | * | 8/2005 | Tajima | 250/423 P |

OTHER PUBLICATIONS

Search Report for International Application No. PCT/US05/21333, dated Oct. 16, 2006.*
Ewald, et al., "Application of Relativistc Laser Plasmas for the Study of Nuclear Reactions," *Plasma Physics and Controlled Fusion* 45, A83-A91 (2003).
Esarey, et al., "Laser Acceleration of Electrons in Vacuum," *Physical Review E* 52, A83-A91 (1995).
Ledingham, "Laser Induced Nuclear Physics and Applications," *Nuclear Physics A* 752, 633c-644c (2005).
Ledingham, "Laser-Driven Photo-Transmutation of $^{129}$I—A Long-Lived Nuclear Product," *Journal of Physics D: Applied Physics* 36, L79-L82 (2003).
Liesfeld, et al., "Nuclear Reactions Triggered by Laser-Accelerated Relativistic Electron Jets," *Applied Phyics B* 79, 1047-1052 (2004).

(Continued)

*Primary Examiner*—Jack Berman
*Assistant Examiner*—Meenakshi S Sahu
(74) *Attorney, Agent, or Firm*—Fish & Richardson P.C.

(57) ABSTRACT

A method and apparatus for accelerating charged particles are disclosed, wherein the method comprises using at least a transverse component of a temporally and spatially shaped electromagnetic field to accelerate one or more charged particles.

29 Claims, 7 Drawing Sheets

OTHER PUBLICATIONS

Magill, et al., "Laser Transmutation of Iodine-129," *Applied Physics B* 77, 387-390 (2003).

Santala, et al., "Production of Radioactive Nuclides by Energetic Protons Generated from Intense Laser-Plasma Interactions," *Applied Physics Letters* 78, 19-21 (2001).

Takashima, et al., "Possibility of Transmutation of $^{135}$Cs by Ultraintense Laser," *Applied Physics Letters* 86, 011501 (2005).

Varin, et al., "Acceleration of Electrons from Rest to GeV Energies by Ultrashort Transverse Magnetic Laser Pulses in Free Space," *Physical Review E* 71, 026601 (2005).

Torchinsky, et al., "Electron Acceleration Through Spatiotemporal Shaping of Ultrashort Light Pulses," *Ultrafast Phenomena XIV* (Springer-Verlag, 2005) pp. 152-154.

Search Report for International Application No. PCT/US05/21333, dated Oct. 16, 2006, by authorized officer David A. Vanore.

* cited by examiner

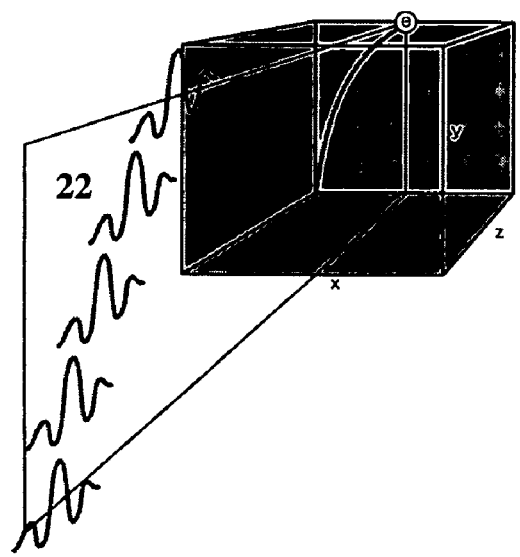
FIG. 3
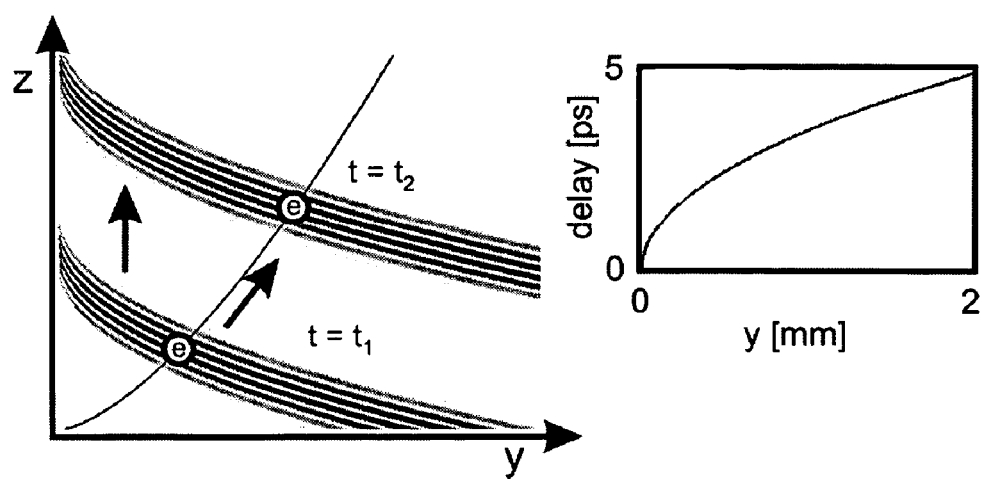
FIG. 4A　　　　　　　　FIG. 4B

ACCELERATION OF CHARGED PARTICLES USING SPATIALLY AND TEMPORALLY SHAPED ELECTROMAGNETIC RADIATION

CROSS-REFERENCE TO RELATED APPLICATIONS

This application claims priority to U.S. Application Ser. No. 60/581,194 entitled "Acceleration of Charged Particles Using Spatially and Temporally Shaped Electromagnetic Radiation", filed on Jun. 18, 2004, the contents of which are incorporated herein by reference.

STATEMENT AS TO FEDERALLY SPONSORED RESEARCH

This invention was made with government support under Grant Number CHE-0212375, awarded by NSF. The government has certain rights in the invention.

TECHNICAL FIELD

This invention relates to accelerating charged particles. For example, the invention relates to accelerating charged particles with spatiotemporally shaped electromagnetic radiation.

BACKGROUND

Accelerated charged particles are used in many applications, including radionuclide production in nuclear medicine, free electron light sources, electron microscopy, electron-beam lithography, and materials characterization by particle beam diffraction. Applications using accelerated charged particles are discussed in, for example, "Laser Induced Nuclear Physics and Applications", *Nuclear Physics A* 752, 633c-644c, 2005 by K. W. D. Ledingham, the contents of which are incorporated herein by reference.

Various methods have been developed for using electromagnetic radiation to accelerate charged particles. Typically, a method for such acceleration involves high intensity pulses of laser light in a configuration wherein the electromagnetic (EM) field takes on both longitudinal as well as the usual transverse oscillation components. A discussion of such methods is given in, for example, "Laser acceleration of electrons in vacuum", *Physical Review E* 52, 5443-5453, 1995 by Eric Esarey, Phillip Sprangle and Jonathan Krall, the contents of which are incorporated herein by reference.

Transverse components of an EM field normally do not yield effective acceleration of charged particles, since each half-cycle of the field causes particle acceleration in a direction opposite to the acceleration produced by the previous half-cycle of the field. Little or no net acceleration of a charged particle results from the passage of the entire EM field through a spatial region containing the particle.

SUMMARY

We disclose a method and apparatus for accelerating charged particles, such as electrons and protons, using one or more transverse components of a spatiotemporally shaped electromagnetic field. One method of exercising such control is the application of pulse shaping techniques in order to produce appropriately tailored EM fields. The accelerated particles are useful for many applications.

In general, in one aspect, the invention features a method which includes accelerating a charged particle using at least a transverse electric field component of a spatially and temporally shaped electromagnetic field.

Embodiments of the method may include any of the following features.

The transverse electric field component of the shaped electromagnetic field may accelerate the charged particle for a period greater than an inverse of an electromagnetic frequency for the shaped electromagnetic field.

A two-dimensional pulse shaper may be used to produce the shaped electromagnetic field from the output of a laser system. The two-dimensional pulse shaper may include at least one dispersive element and a two-dimensional modulator. For example, the modulator may be a liquid crystal spatial light modulator, a microelectromechanical systems device, or a fixed patterned mask. The modulator may operate in a transmissive mode or a reflective mode. In general, the modulator is used to manipulate the amplitude and/or phase of different spatial components of an incident electromagnetic field.

The output of a laser system may be shorter than 1 picosecond or even, shorter than 200 femtoseconds.

The shaped electromagnetic field may include a series of pulses that follow a trajectory of the accelerated charged particle.

The charged particle may be generated from a target material within a reduced-pressure chamber.

The accelerated charged particle may be directed towards a target to produce a radionuclide. For example, the target may include at least one of $^{18}O$, $^{11}B$ and/or $^{63}Zn$. Alternatively, the target may include a substrate with at least one layer of a proton producing material, such as polyethylene.

The accelerated charged particle may be used to induce at least one nuclear reaction in a target. The target may include a material such as $^{129}I$.

Electromagnetic emission may be induced from the accelerated charged particle. The emitted radiation may include radiation at x-ray wavelengths. The emitted radiation may additionally include radiation at ultraviolet wavelengths. For example, the accelerated charged particle may be used to generate bremsstrahlung radiation in a target, such as a high-Z target including $^{181}Ta$ or $^{197}Au$.

The charged particle may be an electron. For example, the accelerated electron may be used as a seed electron in a free electron laser. Alternatively, for example, the accelerated electron may be used for electron microscopy, or electron lithography, or electron diffraction.

The total energy of the accelerated electron may be up to 200 MeV, or up to 600 MeV, or up to 1000 MeV, or more.

The charged particle may be a proton.

In general, in another aspect, the invention features an apparatus including a source of charged particles and a source for providing a temporally and spatially shaped electromagnetic field configured to accelerate at least one of the charged particles using at least a transverse electric field component of the spatially and temporally shaped electromagnetic field.

In general, in another aspect, the invention features an apparatus including: a source of charged particles; a means for accelerating at least one of the charged particles using at least a transverse electric field component of a spatially and temporally shaped electromagnetic field; and a target for the accelerated charged particle.

Embodiments of either apparatus may further include features corresponding to the method recited above.

Advantages of embodiments of the invention may include any of the following.

The acceleration of a charged particle and the final particle energy may be changed by suitably configuring the spatiotemporal pulse shaper.

The distribution of accelerated charged particles may be spatially compact and may have a short temporal duration.

Where electromagnetic emission from accelerated charged particles is induced, for example, by one or more additional fields, the emitted radiation may be very broad bandwidth radiation and may include wavelengths from millimeters to x-ray wavelengths. The emitted radiation may have a short temporal duration, and may be very high intensity radiation. The radiation may further possess a high degree of spatial and temporal coherence.

Unless otherwise defined, all technical and scientific terms used herein have the same meaning as commonly understood by one of ordinary skill in the art to which this invention belongs.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3 is a graph showing the relative disposition of a charged particle and an EM waveform, as the particle propagates in a plane defined by the propagation direction and the polarization of the shaped EM waveform.

FIG. 4A is a graph showing a shaped EM waveform used for charged particle acceleration, and the charged particle position in the plane of propagation, at different times.

FIG. 4B is a graph of the delay time of the shaped EM waveform as a function of the waveform position along the y coordinate direction.

Like reference symbols in the various drawings indicate like elements.

DETAILED DESCRIPTION

Figure 1A:
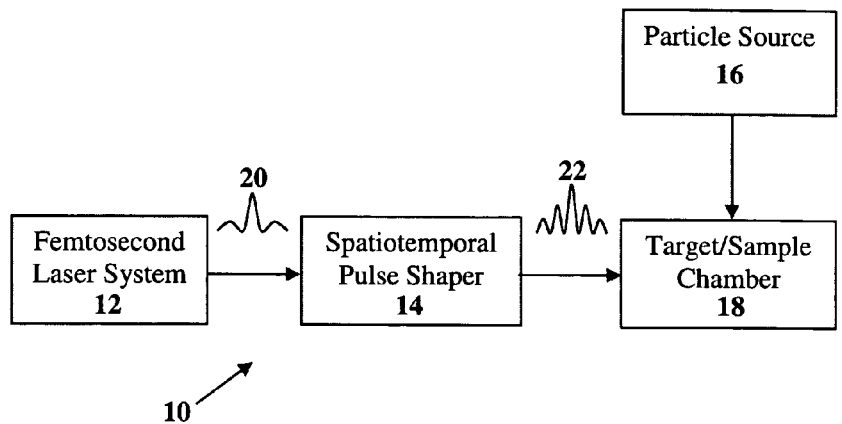
FIG. 1A is a schematic of a system for acceleration of charged particles using spatially and temporally shaped electromagnetic radiation.

FIG. 1A is a schematic of one embodiment of a system 10 for acceleration of charged particles. The embodiment includes a femtosecond laser system 12, a spatiotemporal pulse shaper 14, a particle source 16 and a target/sample chamber 18. Femtosecond laser system 12 generates an electromagnetic waveform 20 which is directed into spatiotemporal pulse shaper 14. Shaper 14 generates output waveform 22 from input waveform 20 by controlling both the spatial and temporal properties of the waveform's electromagnetic field. Output waveform 22 is subsequently directed into target/sample chamber 18.

Particle source 16 introduces one or more particles into chamber 18, and said particles are accelerated by waveform 22 within chamber 18. The accelerated particles are directed onto a target or sample, or may be permitted to exit chamber 18 for use in other applications.

In general, femtosecond laser system 12 may be a laser oscillator, or an amplified laser system, or any other source of electromagnetic radiation suitable for accelerating charged particles. Laser system 12 may provide one or more additional pulses for use in the target/sample chamber 18, and the one or more additional pulses may be phase coherent, and may be temporally synchronized and/or delayed with respect to each other, and with respect to waveform 20.

Input waveform 20 may comprise a single pulse, or more than one pulse.

Suitable embodiments for spatiotemporal pulse shaping are disclosed, for example, in U.S. Pat. No. 5,682,262 entitled "METHOD AND DEVICE FOR GENERATING SPATIALLY AND TEMPORALLY SHAPED OPTICAL WAVEFORMS," the contents of which are incorporated herein by reference.

In embodiments, spatiotemporal pulse shaper 14 may include a two-dimensional liquid crystal spatial light modulator (SLM) and electronic means for controlling the individual pixels of said modulator. The modulator may be configured to operate in reflection mode or in transmission mode. Pulse shaper 14 may additionally include one or more dispersive optical elements, such as a diffraction grating, that disperse the frequency components of input waveform 20 along a first direction of the SLM, with each frequency component being spatially extended along a second direction of the SLM. The SLM may be used to independently modify the phase and/or amplitude of the frequency components of input waveform 20, including independently modifying the spatial components of each frequency component. Following reflection from or passage through the SLM, the dispersed frequency components of waveform 20 may be recombined and spatially overlapped by one or more additional dispersive elements to produce a spatiotemporally shaped output waveform 22. Output waveform 22 may retrace a portion of the optical path followed by input waveform 20, and one or more optical elements may be common to the paths of both input waveform 20 and output waveform 22.

In other embodiments, pulse shaper 14 may include a two-dimensional modulator wherein the modulator comprises a fixed, patterned substrate such as a mask, suitably configured and arranged to impart phase and/or amplitude modulation to an input waveform 20. The patterned substrate may be configured to operate in reflection mode or transmission mode. The optical damage threshold for such a modulator may be much higher than for standard modulators comprising programmable elements, such as a liquid crystal SLM. Pulse shaper 14 may also include one or more dispersive optical elements, such as a diffraction grating, to disperse the frequency components of input waveform 20 along a first direction of the modulator, with each frequency component being spatially extended along a second direction of the modulator. Following reflection from or passage through the fixed modulator, the frequency components of waveform 20 may be recombined and spatially overlapped by one or more additional dispersive elements. The output waveform 22 may retrace a portion of the optical path followed by waveform 20, and one or more optical elements may be common to the paths of both input waveform 20 and output waveform 22.

In embodiments, spatiotemporal pulse shaper 14 may additionally include one or more optical elements to image the output waveform to an image plane at a spatial location, such as a spatial location inside chamber 18, wherein waveform 22 at that location may correspond to a spatial profile of the waveform at the position of the SLM. Alternatively, or in addition, spatiotemporal pulse shaper 14 may include one or more optical elements to image the output waveform to an image plane at a spatial location, such as a spatial location inside chamber 18, wherein waveform 22 at that location may correspond to a Fourier transform of a spatial profile of the waveform at the position of the SLM, such that waveform 22 comprises the spatial wavevector components of a spatial profile of a waveform at the position of the SLM.

In general, spatiotemporal pulse shaper 14 may include at least one modulator, which, as used herein, is an element or combination of elements suitable for modulating the phase and/or amplitude of different spatial components of an incident electromagnetic waveform (which for pulse shaping applications may involve spatially separated frequency components). Examples of modulators include a liquid crystal SLM, a microelectromechanical systems (MEMS) device, a deformable mirror, a fixed patterned substrate, or any other element or combination of elements suitable for modulating the phase and/or amplitude of an electromagnetic waveform. If pulse shaper 14 includes a series of programmable elements, then shaper 14 may also include an electronic controller to adjust said elements.

Further, pulse shaper 14 may include hardware and/or software means to produce, from input waveform 20, an output waveform 22 that is suitable for accelerating charged particles. An iterative process, for example a genetic algorithm, may be used to optimize the configuration of pulse shaper 14 to produce an output waveform 22 which best accomplishes the acceleration. In other embodiments, shaper 14 may include a fixed, patterned substrate which modulates the phase and/or amplitude of an input waveform 20, and wherein the pattern on the substrate has been determined to produce a waveform 22 which suitably accelerates charged particles in the target/sample chamber. The pattern may be optimized prior to fabrication of the patterned substrate. For example, the pattern may be optimized by an iterative numerical calculation.

Output waveform 22 may, in general, have a spatiotemporal profile wherein the interaction between the EM field of waveform 22 and a charged particle accelerates the charged particle. The system 10 may be configured such that the acceleration of one or more charged particles occurs in chamber 18.

Particle source 16 introduces one or more charged or uncharged particles into the target/sample chamber 18 to be accelerated by waveform 22. The particles introduced into target/sample chamber 18 may be ions, such as protons or molecular ions, or may comprise electrons. Alternatively, the particles may comprise electrically neutral atoms or molecules or fragments thereof. More generally, the particles may be elementary particles, such as electrons or positrons, or the particles may comprise one or more atoms of the same or different elements. The particles may further carry electrical charges, or may be electrically neutral. If the particles provided by source 16 are uncharged, the particles are first converted to charged particles before they can be accelerated by waveform 22. For example, the particles may be ionized by one or more additional laser pulses provided by laser system 12, or alternatively, the particles may be ionized by one or more optical pulses provided by another laser source.

Particle source 16 may, for example, comprise a diffusion chamber. Alternatively, particle source 16 may comprise a molecular beam, or an ionization chamber, or a target material in any form. Particle source 16 may be disposed internal to chamber 18, or may be disposed external to chamber 18.

For example, in one embodiment, particle source 16 may comprise a source of electrons derived from a laser-generated plasma, wherein one or more optical pulses generated either by laser source 12 or by another laser source interact with a target, such as a metal target, to generate a plasma comprising one or more free electrons. The free electrons may be accelerated to moderate energies, such as 0.5 MeV, or even 1 MeV, or more, in the plasma. The electrons may then be injected into chamber 18 through an aperture, wherein said aperture may consist of, for example, a thin metal foil with a hole disposed therein. Within chamber 18, the free electrons may subsequently be accelerated by waveform 22.

Chamber 18 provides a controlled environment in which particles introduced by source 16 may be accelerated by waveform 22. For example, chamber 18 may be a reduced-pressure chamber, wherein the ambient pressure may be reduced to less than atmospheric pressure. The ambient pressure within chamber 18 may be reduced to substantially less than atmospheric pressure such that chamber 18 is an ultrahigh vacuum chamber. Alternatively, for example, chamber 18 may be another sealed vessel.

Chamber 18 may additionally include electronic and other apparatus for detecting and measuring properties of accelerated particles, such as particle position, velocity, and energy, and said electronic and other apparatus may be disposed interior or exterior to chamber 18. For example, the chamber may include photographic elements such as a film camera and/or a CCD detector, and a phosphorescent or scintillator screen in order to measure particle position. Alternatively, or in addition, chamber 18 may include detection elements or instruments such as a channeltron, a Faraday cup, or other detection means based upon the deflection of charged particles in a magnetic field.

Charged particles accelerated by waveform 22 may reach energies which are many times greater than their initial energies upon injection by particle source 16 into chamber 18. For example, if individual electrons of energy 0-1 MeV are injected into chamber 18 and accelerated by an optimized waveform 22 of central optical wavelength 1 μm, 1 J pulse energy, 10 fs duration, and focused to a spot size of dimensions 10 μm×2 μm, the individual electrons may be accelerated such that the mean total energy of an electron is up to 200 MeV, or up to 600 MeV, or up to 1000 MeV, or more.

Figure 1B:
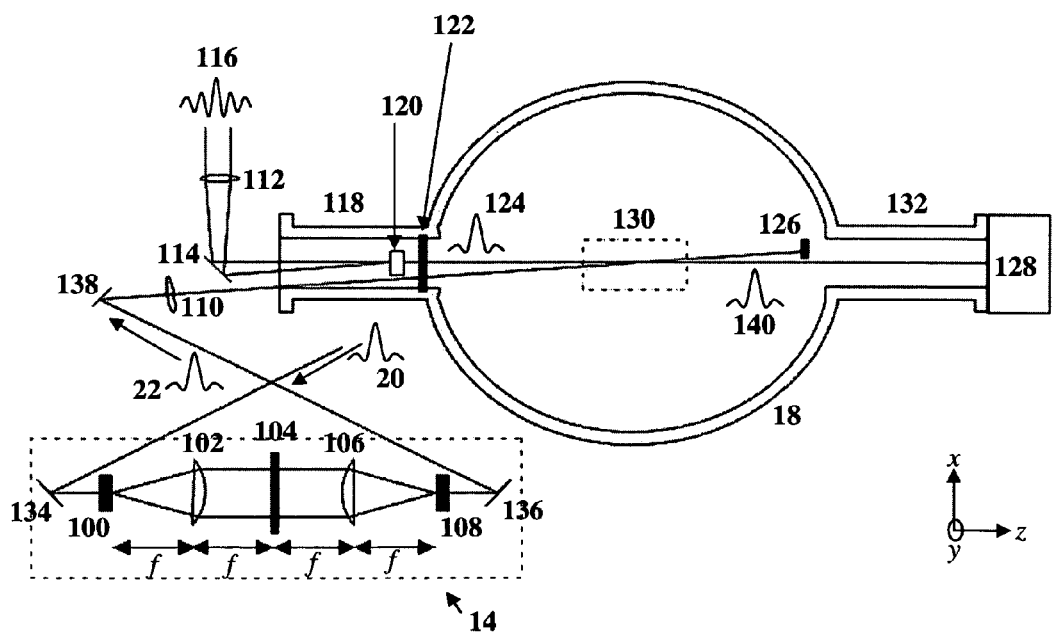
FIG. 1B is a schematic showing a pulse shaper, a particle source, a chamber and a detection apparatus for the acceleration and measurement of charged particles.

FIG. 1B shows one embodiment of pulse shaper 14, particle source 16 and chamber 18. An input waveform 20 generated by laser source 12 enters pulse shaper 14. Waveform 20 is spatially extended in a first direction y and is directed by mirror 134 such that it impinges upon transmissive diffraction grating 100 such that grating 100 disperses the frequency components of waveform 20 in a second direction x different from the first direction. Lens 102 is a cylindrical lens of focal length f, positioned at a distance f from both grating 100 and two-dimensional modulator 104, with curved surface located principally along the x direction. Lens 102 collimates the dispersed frequency components of waveform 20 and focuses each component to its minimum spatial extent at a distance f from lens 102, in the plane of modulator 104.

Modulator 104 includes a two-dimensional element or series of elements which impart phase and/or amplitude modulation to the dispersed frequency components of waveform 20. In the plane of the modulator, each frequency component is located at a particular spatial coordinate position along the x direction of the modulator, and each component is dispersed spatially in the y direction of the modulator. Cylindrical lens 106 of focal length f is positioned at a distance f from modulator 104 and also at a distanced from transmissive diffraction grating 108. Following passage through modulator 104, lens 106 focuses the frequency components of the waveform such that the components are spatially overlapped at the position of grating 108. Upon passage through grating 108, the frequency components of the output waveform 22 remain spatially coincident.

Suitable configuration of modulator 104 yields an output waveform 22 that may be both temporally and spatially shaped relative to the spatiotemporal profile of input waveform 20. The spatiotemporal profile of waveform 22 may be adjusted such that waveform 22 is optimally designed for accelerating charged particles. In the embodiment of FIG. 1B, following reflection from mirrors 136 and 138, waveform 22 is focused by spherical lens 110 into a region 130 within chamber 18 that represents the interaction region. Within region 130, waveform 22 accelerates particles introduced into chamber 18 by particle source 16.

In the present embodiment, a second waveform 116 generated either by laser source 12 or by another laser source is focused by lens 112 and reflected by mirror 114 onto the surface of a solid target material 120. Target 120 may include, for example, materials such as graphite, aluminum, titanium, or other materials. The composition of target 120 depends upon the type of particles desired for injection into target/sample chamber 18. For instance, in order to generate protons for acceleration, target 120 may include a 1 mm thick graphite substrate with a 2-3 μm thick layer of polyethylene.

Waveform 116 impinges upon target 120 and generates one or more charged particles which propagate substantially in the direction of waveform 116. The particles enter chamber 18 by passing through aperture 122. The aperture may comprise, for example, a thin metal film with a small hole therein, oriented such that only charged particles with trajectories that differ from the propagation direction of waveform 116 by very small amounts pass through the small hole.

Particle distribution 124 includes the set of charged particles which successfully pass through aperture 122 and enter chamber 18.

Particles 124 are subsequently accelerated by waveform 22 within the interaction region 130 of chamber 18, yielding a distribution of accelerated charged particles 140. Block 126 is disposed such that it intercepts and scatters waveform 22 following passage through the interaction region 130. Analyzer 128 is disposed relative to the trajectories of particles 140 such that various properties of the accelerated charged particles 140 may be measured. For example, analyzer 128 may include a scintillator and a film camera or CCD device for measuring the spatial distribution of the accelerated particles. Alternatively, or in addition, for example, analyzer 128 may include a hemispherical analyzer for measurement of the energies of accelerated charged particles, and/or a channeltron, and/or a Faraday cup.

In general, diffraction gratings 100 and 108 in FIG. 1B may include any element or series of elements which are oriented or configured to disperse the frequency components of input waveform 20 in a second direction x. For example, transmissive grating 100 may be replaced by a prism or a reflective diffraction grating. Lenses 102 and 106 may, in general, have any focal length, and the focal lengths of the two lenses may be the same or different, providing the arrangement of gratings 100 and 108, and lenses 102 and 106, is such that the frequency components of waveform 20 are dispersed along a second direction x and focused to the minimum spatial extent in the x direction at the position of modulator 104. Lenses 102 and/or 106 may also be reflective cylindrical mirrors.

Modulator 104 may include a fixed element, such as a patterned glass mask. Alternatively, for example, modulator 104 may include a programmable device such as a 2D SLM, a 2D MEMS device, or a 2D deformable mirror. Modulator 104 may also include an electronic controller for programming the individual elements of the device.

Modulator 104 may be configured to operate in either reflection mode or transmission mode. If modulator 104 operates in reflection mode the input waveform 22 may approximately retrace its original path upon reflection from modulator 104. Pulse shaper 14 may then additionally include a beamsplitter, mirror, or other element to divert output waveform 22 in the direction of the input port 118 of chamber 18.

Lens 110 may be transmissive or reflective (e.g., a curved mirror having optical power), and its focal length may be chosen to produce optimum acceleration of charged particles within chamber 18. Lens 112 focuses waveform 116 onto target 120, and the orientation and focal length of lens 112 may be selected to produce a high yield of charged particles from the target material. Lens 112 may be transmissive or reflective.

Waveform 116 may include one or more optical pulses, and may be generated by laser source 12 or by another laser source. The one or more pulses may be phase coherent and may be temporally synchronized or delayed with respect to waveform 20. For example, waveform 116 may include two pulses, the first being less intense for generating a plasma in target 120, and the second being more intense for accelerating electrons or ions within the plasma. Waveform 116 may accelerate charged particles generated from target 120. For example, particles entering chamber 18 may have energies of 0.5 MeV, or 1 MeV, or more.

Analyzer 128 may include any instrument or combination of instruments or devices suitable for characterizing one or more properties of the accelerated charged particles. Alternatively, analyzer 128 may be replaced by an apparatus including a target or sample and a holder or other such support/manipulation structure for said target or sample. For example, analyzer 128 may be replaced by a target material including an element such as $^{11}$B, $^{18}$O, $^{63}$Cu, or another material, for example, for use in generating radionuclides, as described further below. Analyzer 128 may, alternatively, be removed and chamber 18 coupled to another vessel via output port 132.

In embodiments, the charged particle may be accelerated in a direction that is determined by the combined forces due to the electric and magnetic field components of output waveform 22. The optimal field that accomplishes the acceleration of the charged particle may be calculated by solving the relativistic equations of motion for a charged particle in an EM field. For an EM field propagating in the z-direction and polarized in the y-direction, the motion of the charged particle is confined to the y-z plane. The pulse delay is given as $$\Delta t(y) = t(y) - \frac{z(y)}{c} \quad (1)$$

Knowing the delay as a function of y, the ideal EM field is given by $$E(x, y, t) = E_1(x) E_2(y, t + \Delta t(y)) \quad (2)$$

If a constant field $E(y)=E_0$ is assumed switched on at $t=0$ and switched off at some later time, then the expression for the pulse delay as a function of they coordinate for a particle bearing a single negative or positive charge is $$\Delta t = \sqrt{\frac{2m_0 y}{eE_0}} \quad (3)$$

where $m_0$ is the particle rest mass and e the elementary charge.

In typical embodiments, a charged particle may be injected into chamber 18 such that its initial trajectory is at an angle θ to they axis in the y-z plane. For a particle with an initial energy of 1 MeV, for example, a typical injection angle θ may be 45-65°.

Figure 2A:
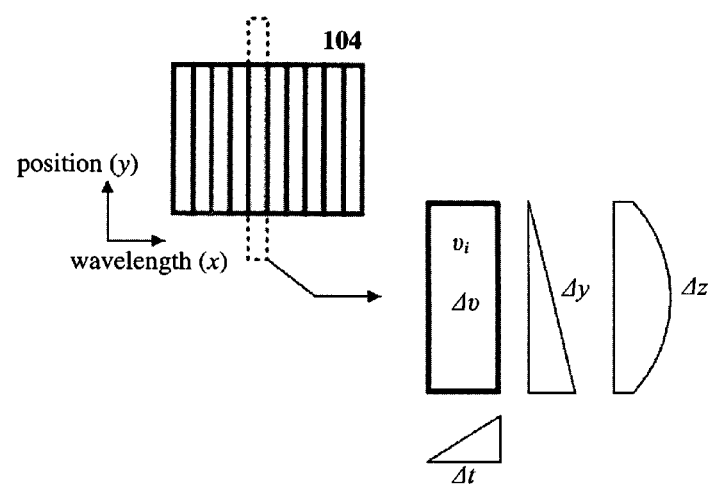
FIG. 2A is a schematic of a two-dimensional modulator configured to produce a waveform suitable for accelerating charged particles.

FIG. 2A is a schematic of a two-dimensional modulator that may be used, for example, in the embodiment of FIG. 1B in order to produce a suitable output waveform 22 for accelerating charged particles. The frequency components of input waveform 20 are dispersed along the wavelength, or x, direction of the modulator, with each wavelength component spatially extended in the spatial, or y, direction of the modulator. The right side of FIG. 2A shows an expanded schematic of a particular two-dimensional section of the modulator. If the modulator includes a series of discrete elements, such as a liquid crystal SLM with discrete pixels, then the section shown includes a subset of the total number of modulator elements. Alternatively, if the modulator includes a single continuous element such as a fixed glass mask, then the section shown represents a section of the modulator surface which interacts with an impinging waveform.

In the x direction, the section of the modulator active area shown in the expanded view includes a frequency bandwidth $\Delta v$ and a central frequency $v_i$, where the frequency bandwidth $\Delta v$ is dependent upon, for example, the bandwidth of input waveform 20, the structure of diffraction grating 100, lens 102, and the size of the section relative to the overall size of the modulator. In order to produce a waveform 22 suitable for accelerating charged particles, modulator 104 is used to impart phase and/or amplitude modulation to the spatially and spectrally dispersed waveform 20. For example, modulator 104 may be a phase-only modulator, and may be used to impart a linear phase retardation in the x direction to the dispersed frequency components of input waveform 20. A linear phase retardation applied in the x direction to the expanded portion of modulator 104 shown on the right side of FIG. 2A shifts the portion of the output waveform 22 that corresponds to the expanded region either forward or backward in time by an amount Δt. A linear phase retardation may also be applied in the y direction of the modulator, which shifts the portion of output waveform 22 that corresponds to the expanded region to a different spatial location along the y axis by an amount Δy. In addition, a parabolic retarding phase may be introduced by modulator 104 along the y direction in order to control the position of the focal plane of the portion of output waveform 22 which corresponds to the expanded section in FIG. 2A. For a given parabolic phase contribution, the position of the expanded portion's focal plane along the propagation direction of waveform 22 is displaced by an amount Δz. In typical embodiments, the focal plane of a portion of output waveform 22 may be displaced by up to 1 mm, or up to 10 mm, or more.

In general, the phase retardation applied in either the x or y directions may have a complex profile. The modulator 104 may be a fixed modulator, or may be an adaptive modulator such as a liquid crystal SLM, a MEMS device, or a deformable mirror, and modulator 104 may additionally include optical elements such as lenses, beamsplitters, polarizers, waveplates and diffraction gratings.

Figure 2B:
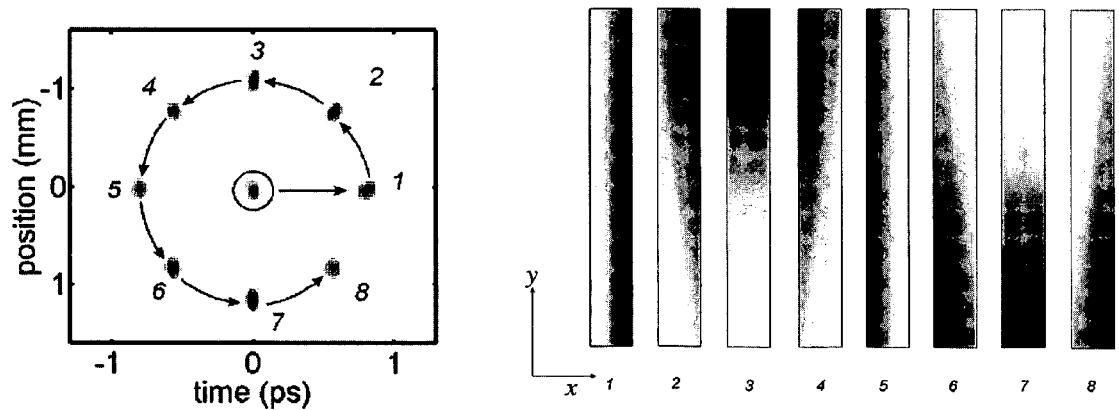
FIG. 2B is a diagram showing the configuration of a two-dimensional modulator in a spatiotemporal pulse shaper and the effect of changing a phase modulation imparted by the modulator to an incident waveform.

FIG. 2B illustrates the results of introducing linear phase retardation in both the x and y directions of modulator 104 via an adaptive two-dimensional SLM in pulse shaper 14. The right side of FIG. 2B illustrates eight different phase retardation configurations of modulator 104, numbered consecutively. Each of the numbered rectangular regions represents a subset of the active area of modulator 104 on which spatially- and spectrally-dispersed waveform 20 impinged. Only that portion of waveform 20 impinging on the subset region of modulator 104 was used in the measurement shown on the left side of FIG. 2B.

A phase shift was applied by modulator 104 in the subset region in order to change the temporal delay and/or the spatial position of the output portion of waveform 22 which corresponded to the subset region. The phase shifts imparted by the modulator are shown on each of the eight representations of the subset region, wherein the phase shift, modulo 2π, at a particular spatial location is denoted by a grayscale value ranging from white (zero phase shift) to black (π radians phase shift). Each of the eight subset regions on the right side of FIG. 2A corresponds to a particular measured output waveform 22 on the left side of the figure.

The left side of FIG. 2B illustrates a spatially resolved cross-correlation measurement of output waveform 22. With a uniform phase retardation applied by modulator 104 in both the x and y directions, output waveform 22 was located at time zero and position zero in the graph. The position of output waveform 22 in both time and space was shifted by applying linear phase shifts in either or both of the x and y directions of the modulator. For example, in order to shift output waveform later in time (position 1), a linear phase shift was applied in the x direction by the modulator 104, as shown on the right side of FIG. 2B. In order to shift output waveform 22 earlier in time by the same amount (position 5), a linear phase shift of the same amount but opposite orientation was applied by modulator 104, as shown on the right side of FIG. 2B. Shifting output waveform 22 up (position 3) and down (position 7) along they axis was accomplished by applying a linear phase shift in they direction via modulator 104, as shown.

In embodiments wherein modulator 104 includes a series of individual, programmable elements, such as a liquid crystal SLM, the active area of the modulator may be divided into a series of sections oriented along they direction of the modulator, wherein the phase and/or amplitude of that portion of dispersed waveform 20 which impinges upon a particular section may be adjusted in two dimensions, in order to control the spatiotemporal properties of the corresponding portion of output waveform 22. The active area of modulator 104 may be divided into 5 or more sections along the y direction of the modulator, such as 10 sections, or 50 sections, or 100 sections, or 250 sections, or more.

In other embodiments wherein modulator 104 includes a fixed mask, such as a patterned glass mask, the phase retardation profile may vary continuously across the surface of the mask in the x and/or y directions.

Figure 2C:
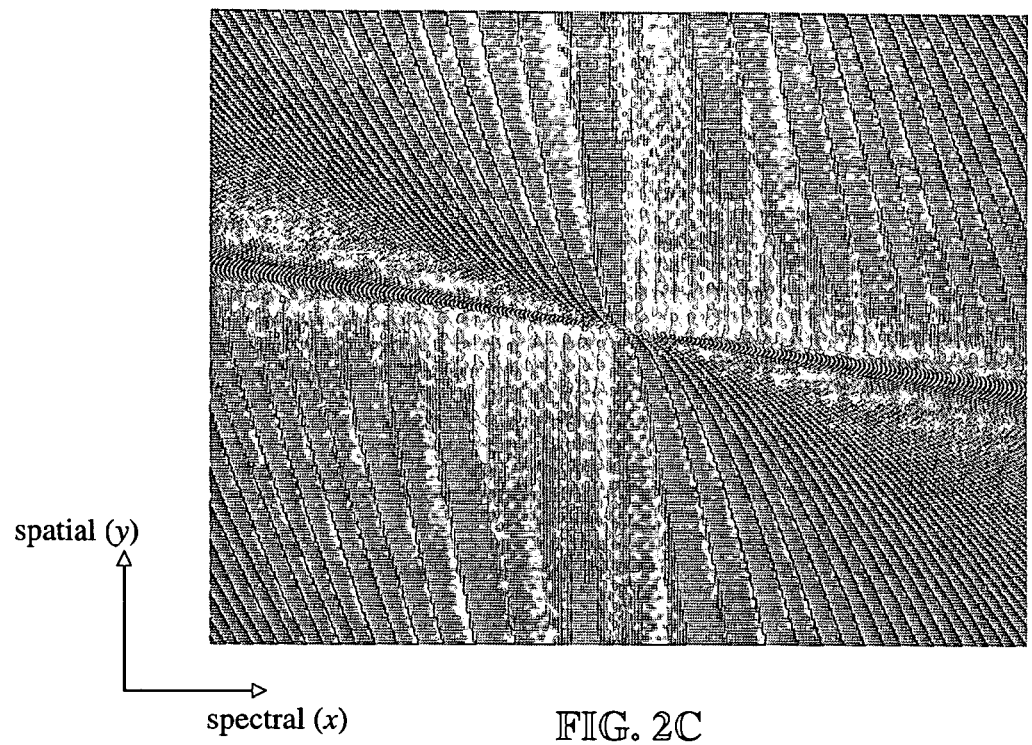
FIG. 2C is a schematic of a two-dimensional modulator showing the phase retardation imparted by the modulator to an impinging waveform at each spatial location on the surface of the modulator.
Figure 2D:
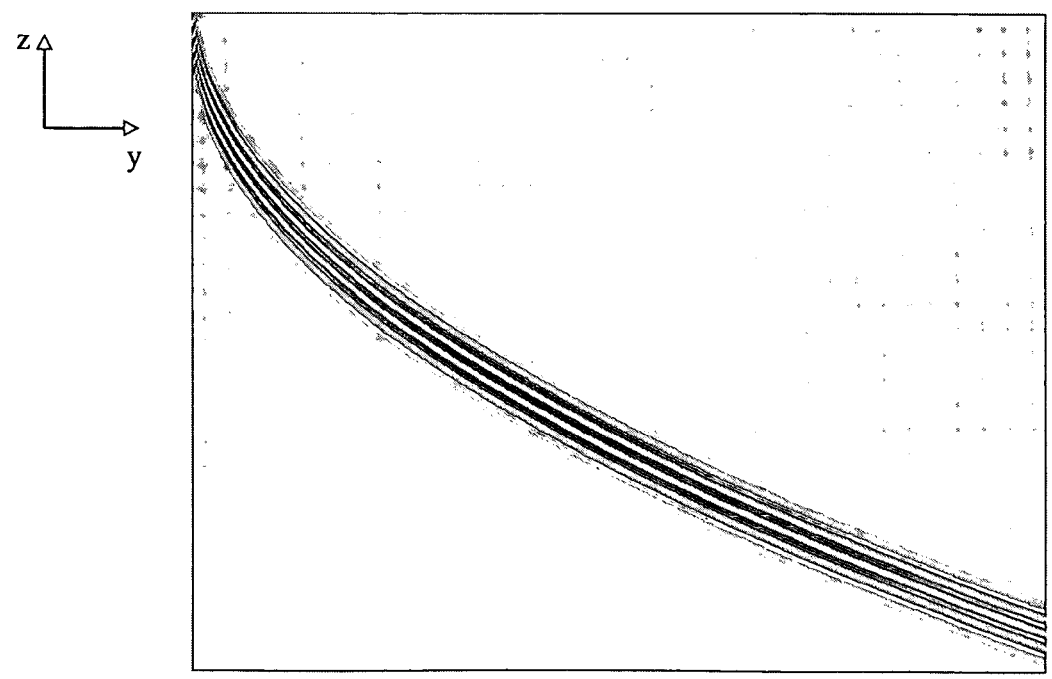
FIG. 2D is a graph showing a waveform which results from the passage of a spatially Gaussian pulse through a two-dimensional spatiotemporal pulse shaper including a modulator configured as in FIG. 2C.

FIG. 2C shows a schematic of a computer simulated two-dimensional phase retardation profile imparted by modulator 104 to spatially- and spectrally-dispersed input waveform 20 in a typical embodiment, in order to produce an output waveform 22 suitable for accelerating charged particles. The phase delay introduced by the modulator at a given spatial location is represented by the grayscale intensity value at that location, wherein the phase shift range, modulo $2\pi$, extends from white (zero phase shift) to black ($\pi$ radians phase shift). FIG. 2D is a graph showing the computer simulated spatiotemporally shaped output waveform 22 which results from introducing a spatially Gaussian initial waveform 20 of duration 10 fs and central wavelength 800 nm into pulse shaper 14, wherein modulator 104 is configured as in FIG. 2C. The electric field of output waveform 22 in the transverse y direction, i.e. in a direction orthogonal to the propagation direction, is represented on an intensity grayscale, wherein the field's minimum intensity is colored white and the maximum intensity is colored black. Intermediate intensity values are interpolated between these limits.

The waveform shown in FIG. 2D has a substantially curved wavefront, which is useful for the early stages of acceleration of a charged particle. The maximum attainable curvature in the wavefront is dependent upon the spatial resolution of modulator 104. The shape of the waveform 22 results from the correspondence between space and time for a propagating waveform. A charged particle, such as an electron, that is injected into chamber 18 and that interacts with waveform 22 will encounter different portions of waveform 22 at different times or equivalently, in different regions of space. If output waveform 22 was unshaped relative to input waveform 20, then output waveform 20 would appear as an oscillating field along the z-axis, and extending horizontally along the y-axis, with no additional wavefront tilt in the z-direction. The overall interaction time between such a waveform and the charged particle may be limited to the transit time of the charged particle through the relatively narrow spatial region comprising the EM field.

The shaped output waveform 22 shown in FIG. 2D extends the interaction time between the waveform and the charged particle, since the spatial configuration of the waveform is designed to follow a trajectory of the charged particle as it is accelerated in the y-z plane. In the figure, at the earliest interaction times, the charged particle encounters that portion of waveform 22 represented in the upper left corner of the figure. As the charged particle is accelerated, its trajectory of motion includes components in both the z and y spatial directions. Shaped waveform 22 follows this trajectory towards the lower right corner of the figure, such that the charged particle "surfs" along the wavefront of the waveform, and acceleration occurs along the entire length of the wavefront traversed by the charged particle.

FIG. 3 shows an embodiment wherein computer simulated waveform 22 is shaped such that a portion of the waveform's electric field coincides with the position of one or more particles to be accelerated for a duration greater than an inverse frequency of the EM field comprising waveform 22. For example, waveform 22 in FIG. 3 may comprise a series of temporally and spatially offset pulses that may be positioned such that portions of the electric field with the same sign follow the trajectory of the accelerated particle. In the simulation corresponding to this figure, an initial Gaussian pulse of duration 10 fs and central wavelength 800 nm was used to calculate output waveform 22.

FIG. 4A shows the computer simulated position of a charged particle along with the simulated transverse electric field component of waveform 22 in the y-z plane at different times. The electric field is represented on a grayscale range, wherein the minimum field amplitude is white, the maximum field amplitude is black, and intermediate field amplitudes are interpolated grayscale values. The charged particle propagates with respect to the spatiotemporally shaped EM-field such that the charged particle and the maximum field amplitude remain temporally and spatially coincident for a duration greater than an inverse frequency of the shaped EM field. An initial Gaussian waveform of duration 10 fs and central wavelength 800 nm was used to calculate output waveform 22.

FIG. 4B shows the calculated delay of the spatiotemporally shaped EM field as a function of position along they direction. The pulse delay is calculated relativistically in Equation (3), but in this case the same result would be obtained in a non-relativistic calculation, since the relativistic portion—especially the magnetic contribution to the trajectory—cancels for the assumption of a constant field.

In embodiments, as the field strength is increased, the time and distance necessary for acceleration of a charged particle to a particular final energy decrease. The upper limit of the field strength is determined by the spatial resolution of spatiotemporally shaped output waveform 22, not by radiation damping effects. For example, the final total energy of an electron accelerated by an EM field at the upper limit of its strength may be as high as 200 MeV, or as high as 600 MeV, or as high as 1000 MeV, or more.

High spatial resolution is most important during the initial phase of acceleration, when the output waveform 22 is curved in the y-z plane, as shown in FIG. 4A. As the accelerated particle attains higher kinetic energies, waveform 22 approaches a linear slope in the y-z plane.

Figure 5:
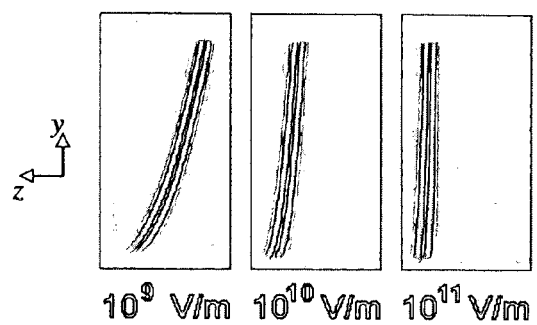
FIG. 5 is a graph showing the shape of an EM waveform, as a function of the electric field amplitude, for use to yield a charged particle with a particular energy following acceleration.

In order to accelerate a charged particle from an initial energy to a particular final energy using one or more transverse components of an electric field, a shaped EM waveform 22 as shown, for example, in FIG. 4A may be used. The amount of curvature of the EM waveform is limited by the resolution of pulse shaper 14. In order to accelerate charged particles to higher energies at a particular field strength, more curvature of waveform 22 may be required. The spatial resolution of pulse shaper 14 may limit the amount of acceleration that can be achieved at a particular field strength for a given charged particle. Demands on the resolution of shaper 14 may be relaxed, for example, by utilizing higher field strengths as shown in FIG. 5. The transverse components of the electric fields of output waveform 22 are shown for three different field strengths, each of which is employed to accelerate a charged particle from the same initial energy to the same final energy. The fields are represented on a grayscale range, wherein the minimum field amplitude is white, the maximum field amplitude is black, and intermediate field amplitudes are interpolated grayscale values. At the highest field strength $10^{11}$ V/m, the initial curvature of the field is reduced since the force due to the electric field components on the charged particle, including the force at the earliest times during the interaction, is greater.

Figure 6:
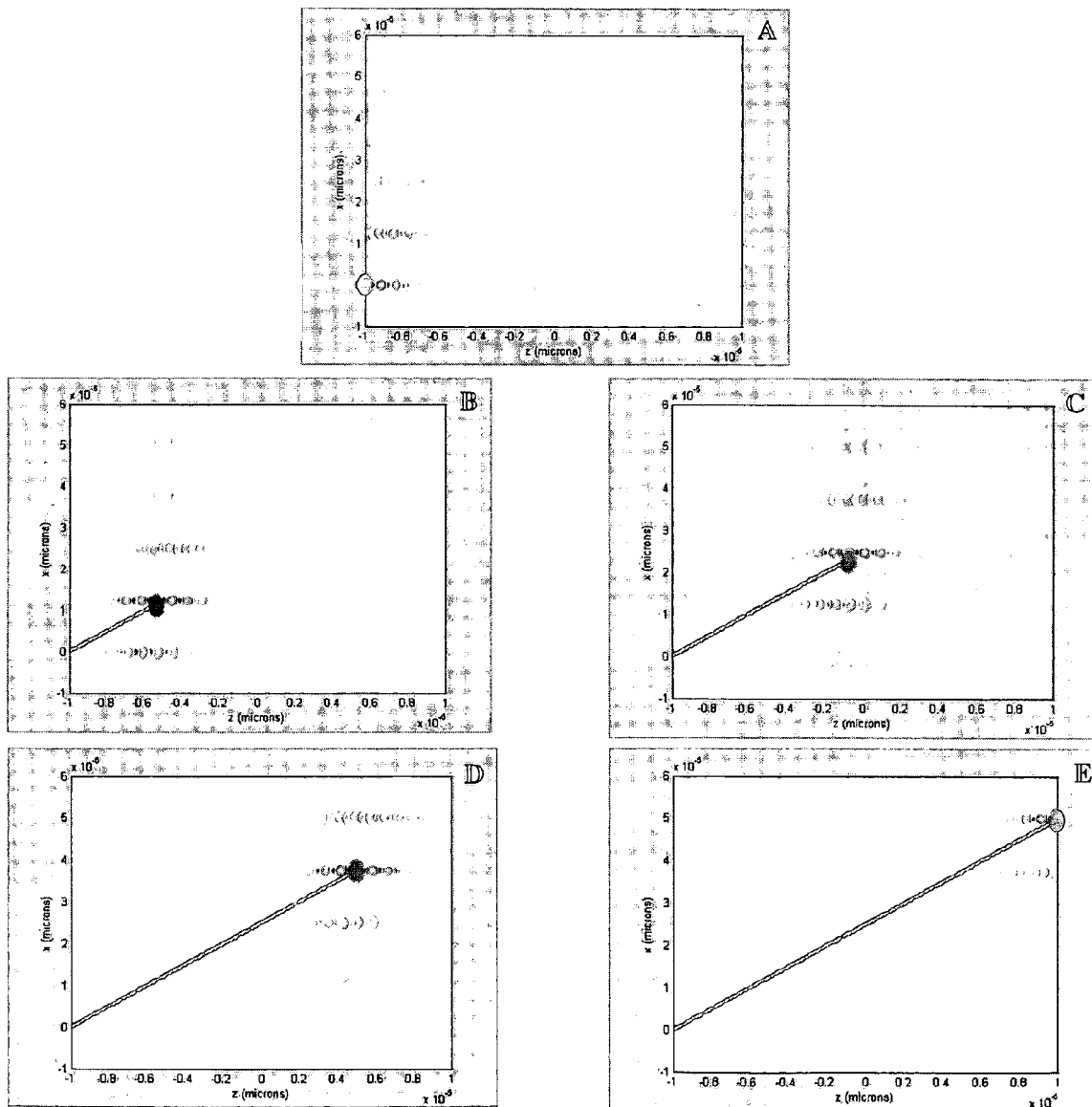
FIG. 6 is a series of graphs that demonstrate the acceleration of an electron by means of a shaped EM waveform including five distinct, spatially localized pulses.

FIG. 6 shows an example of an embodiment wherein a computer simulated adaptive modulator includes a series of discrete elements, such as a two-dimensional liquid crystal SLM, is used in pulse shaper 14 to produce output waveform 22. The modulator is divided into sections oriented along the y direction, and each portion of spatially dispersed input waveform 20 impinging upon a given section is independently modified by modulator 104. In the present embodiment, the modulator is divided into 100 sections. Five equally spaced portions of spatially dispersed input waveform 20, corresponding to five equally spaced sections of modulator 104, are combined to yield output waveform 22. Frames A-E of FIG. 6 show an electron as a black dot propagating in a plane defined by the propagation and polarization directions of waveform 22, wherein the five portions of output waveform 22 successively accelerate the electron. The electron trajectory in the plane is represented by a white line. The transverse component of the electric field of waveform 22 is shown in each frame in a grayscale representation, wherein the minimum field amplitude is white, the maximum field amplitude is black, and intermediate amplitudes are interpolated grayscale values. A phase shift is applied in the spectral direction of modulator 104 in order to retard the five portions of output waveform 22, such that the five portions each remain temporally coincident with the electron along its trajectory. A phase shift is applied in the spatial direction of modulator 104, such that the five output portions comprising waveform 22 are vertically displaced from one another, and such that each is spatially coincident with the electron along its trajectory. An additional phase shift, which may be substantially parabolic in form, is applied by modulator 104 in order to shift the focal plane of each of the five portions of output waveform 22, such that each portion is substantially focused to its minimum extent when that portion is temporally and spatially coincident with the electron.

Figure 7:
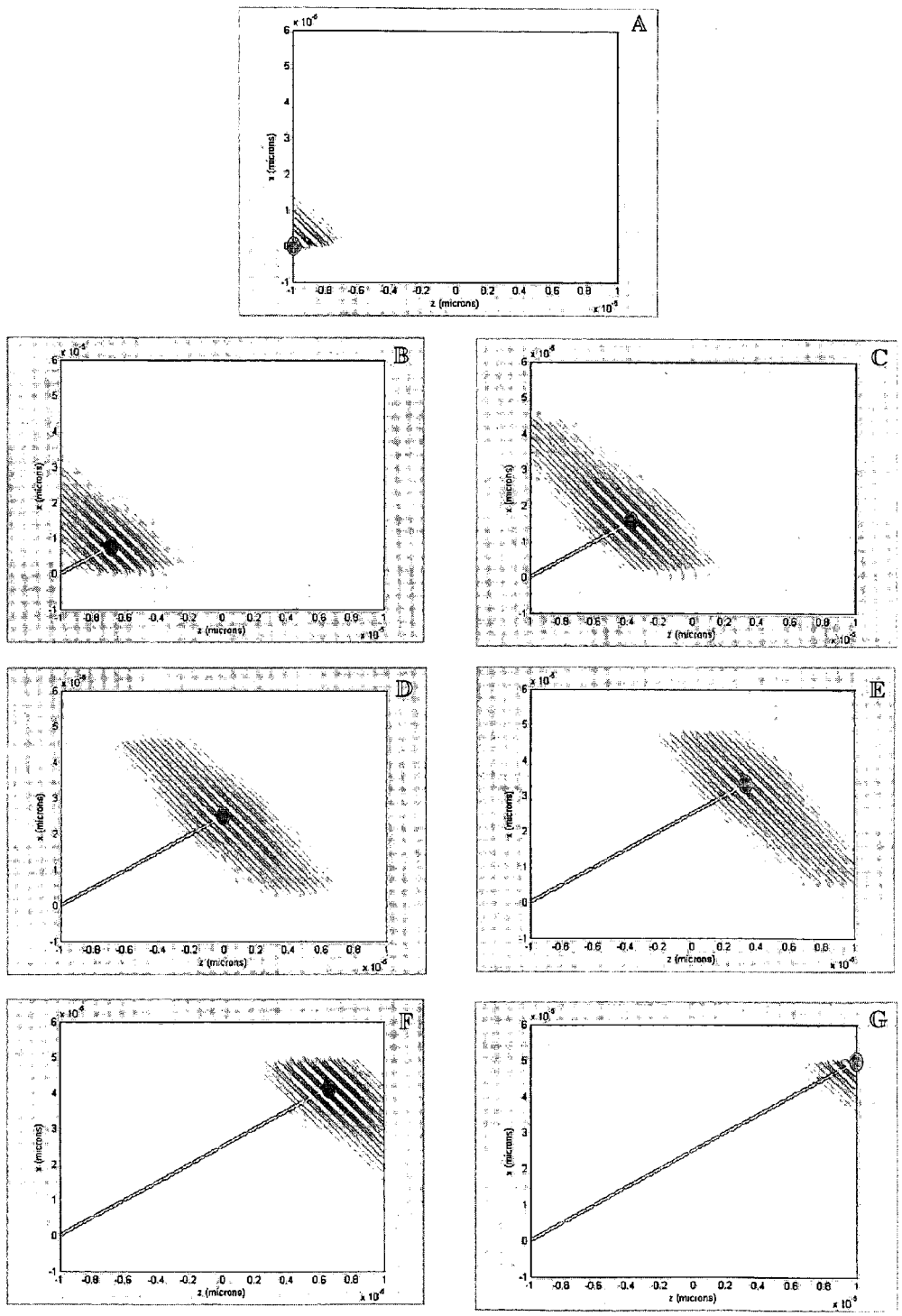
FIG. 7 is a series of graphs that demonstrate the acceleration of an electron by means of a shaped EM waveform comprising 100 distinct, spatially localized pulses.

FIG. 7 illustrates an embodiment similar to the embodiment of FIG. 6, wherein a computer simulation includes 100 equally spaced portions of spatially dispersed input waveform 20, each corresponding to a vertical section of modulator 104, and each of which are adjusted independently by modulator 104 and subsequently combined to yield output waveform 22. The overall acceleration of the electron in this embodiment may be larger than in the embodiment of FIG. 6. The transverse component of the electric field of waveform 22 is represented on a grayscale similar to that of FIG. 6, and the electron is represented as a black dot with a white line showing the electron's trajectory in the plane of propagation. Frames A-G show the relative dispositions of the electron and output waveform 22 as the electron is accelerated by the EM field of the waveform.

The one or more accelerated particles may be directed towards a target or sample area within chamber 18, or may be permitted to exit chamber 18 for use in other applications. In some embodiments, the one or more accelerated charged particles may be further manipulated by applied electric and/or magnetic fields following acceleration by output waveform 22. For example, in some embodiments, one or more additional magnetic fields may be used to cause the accelerated charged particles to oscillate in a well defined way, thereby inducing emission of coherent radiation at the oscillation frequency. In other embodiments, for example, one or more magnetic fields may be used to bend the trajectories of accelerated charged particles, such as electrons, resulting in the emission of radiation by the charged particles. The emission of said radiation may occur, for example, along a direction radially outward from the center of the arc of curvature of the particle trajectory.

In embodiments wherein accelerated charged particles are made to oscillate through the application of one or more additional magnetic fields, or wherein magnetic fields are used to bend the trajectories of accelerated charged particles, the spectral range of the emitted radiation may be extremely wide, ranging from wavelengths of many millimeters to x-ray wavelengths. The emitted radiation may possess a high degree of spatial and/or temporal coherence. The radiation may be focused to a diffraction limited spot size defined by its wavelength. Further, the radiation may be very high intensity radiation, and may have a very short temporal duration.

The wavelength, duration, intensity, phase profile, amplitude profile, and/or other properties of the emitted radiation may be changed through iterative optimization of the configuration of pulse shaper 14, or alternatively by calculating the optimum spatiotemporal profile of output waveform 22 a priori and configuring pulse shaper 14 to produce the optimum output waveform 22.

In embodiments wherein the one or more charged particles are directed toward a target or sample area, the one or more charged particles may irradiate and/or interact with a sample or target mounted inside chamber 18. One or more additional optical pulses may be produced by, for example, laser system 12 or another laser, and said pulses may be used for irradiation of the target or sample. Said pulses may be phase coherent, and may be time-synchronized or temporally delayed with respect to input waveform 20 and the one or more accelerated charged particles.

Figure 8:
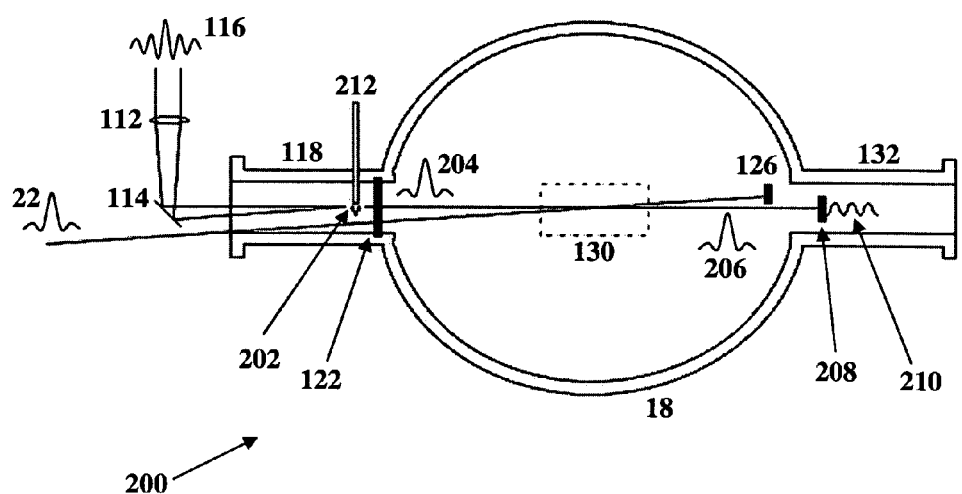
FIG. 8 is a schematic of a system for generating bremsstrahlung radiation using accelerated charged particles.

In other embodiments, accelerated charged particles may be used to generate electromagnetic radiation by direct bombardment of a target material. For example, FIG. 8 is a schematic of one embodiment of an apparatus 200 for the generation of bremsstrahlung by using electrons accelerated by a spatiotemporally shaped waveform. Lens 112 and mirror 114 focus and direct waveform 116 into the input port 118 of chamber 18. Gas particles 202, such as helium gas atoms, are introduced into input port 118 through nozzle 212 of a gas jet. Waveform 116 ionizes the helium atoms, producing helium ions and free electrons. The free electrons are subsequently accelerated to moderate energies by waveform 116 and enter chamber 18 through aperture 122. Particle distribution 204 includes a distribution of electrons with trajectories lying principally along the propagation direction of waveform 116.

The electrons comprising distribution 204 are subsequently accelerated by a suitably generated waveform 22 to yield accelerated particle distribution 206 which impinges upon target 208 mounted within chamber 18. Target 208 may include any material suitable for bremsstrahlung generation via direct electron bombardment. For example, target 208 may include a high-Z target such as $^{181}$Ta or $^{197}$Au.

Upon irradiation with accelerated electron distribution 206, target 208 emits bremsstrahlung radiation 210 in a direction principally along the direction of propagation of distribution 206. The emitted radiation may comprise a broad band of frequencies. For example, the radiation may comprise frequencies in the x-ray and ultraviolet region of the electromagnetic spectrum. The radiation 210 may, additionally, be detected via suitable detection means mounted to, for example, output port 132. Alternatively, the radiation may exit chamber 18 through port 132 and be used in another application.

Charged particles accelerated by waveform 22 may alternatively be used, for example, to induce nuclear reactions in target chamber 18. Induced nuclear reactions may be useful for applications such as the production of radioactive isotopes for medical imaging, such as for the production of positron-emitting isotopes suitable for use in Positron Emission Tomography (PET). Typically, PET diagnostic imaging includes injecting a patient with a pharmaceutical labeled with one or more short lived, positron-emitting isotopes such as $^{11}$C, $^{13}$N, $^{15}$O, $^{18}$F, or others. For example, a commonly used radio-pharmaceutical is 2-fluoro-2-deoxy-glucose, 2-[$^{18}$F]FDG. Radio-pharmaceuticals collect in active areas of the body such as tumors, and the bio-distribution of labeled species may be determined by time-resolved PET imaging. PET-FDG may be more successful than conventional x-ray computed tomography in diagnosing certain types of cancer, such as lung cancer.

Figure 9:
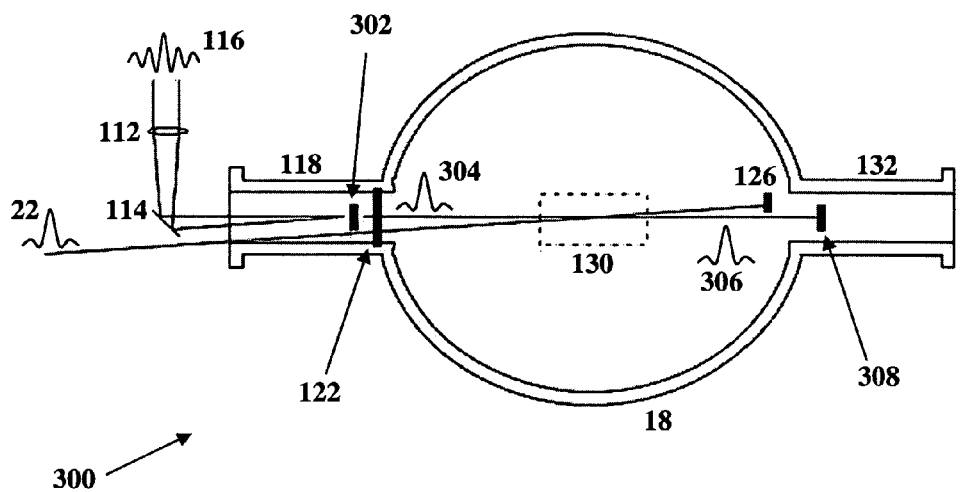
FIG. 9 is a schematic of a system for radionuclide production using accelerated charged particles.

Radioactive isotopes for PET are typically produced by irradiation of a suitable natural or enriched target with high energy protons derived from a cyclotron or van de Graaf generator. The infrastructure associated with such particle sources is expensive to build and maintain. One embodiment of an alternative system 300 for radionuclide production for applications such as PET is shown in FIG. 9. The system includes a chamber 18 with an input port 118 and an aperture 122 which separates the port from the chamber. Aperture 122 may be, for example, a thin metal film with an opening therein. Waveform 116, which may include one or more pulses, is focused by lens 112 and directed by mirror 114 onto the surface of target 302 which may be disposed, for example, interior to input port 118. In the present embodiment, target 302 includes a material suitable for producing free protons. For example, target 302 may include a substrate such as graphite, aluminum, titanium, BK-7 glass, or other substrate material, with one or more layers disposed thereon, wherein the layer or layers may include materials such as polyethylene. Irradiation of target 302 with waveform 116 may produce one or more free protons suitable for subsequent acceleration. Without wishing to be bound by theory, it is believed that the free protons arise from a strong electric field created by migration of a dense electron cloud in response to waveform 116.

The one or more protons liberated from target 302 may also subsequently experience some additional acceleration due to waveform 116. For example, waveform 116 may include two pulses, the first of which is designed to produce free protons and the second which accelerates the protons to moderate energies. In the present embodiment, one or more protons pass through aperture 122 and enter chamber 18. Spatiotemporally shaped waveform 22 also enters chamber 18 and accelerates the proton distribution 304 therein in the interaction region 130 to produce accelerated proton distribution 306. Protons 306 subsequently impinge upon transmutation target 308 in order to convert the target material to a useful isotope. For example, positron-emitting isotopes such as $^{18}$F may be produced from a target 308 enriched with $^{18}$O for use in PET imaging. Alternatively, for example, $^{11}$C may be produced from a target 308 which includes $^{11}$B, or $^{63}$Cu may be produced from a target 308 including $^{63}$Zn.

In general, system 300 may be employed to induce nuclear reactions in other materials as well. For example, system 300 may be configured to convert long-lived radionuclide targets 308 such as $^{129}$I to short-lived radionuclides such as $^{128}$I. Radionuclides comprising target 308 may result from, for example, nuclear fission processes, and the conversion to shorter-lived species may provide means for safer long-term storage of these nuclides.

When the charged particles accelerated by waveform 22 comprise electrons, said electrons may be used as seed sources for linear accelerators, free-electron lasers, and other research instruments. For example, accelerated electrons may be used in electron microscopes, electron diffraction instruments including ultrafast time-resolved electron diffraction instruments, and other instruments for materials characterization.

In other embodiments wherein the charged particles are electrons, the accelerated electrons may be used in electron lithography systems for materials fabrication.

More generally, the technique may be used to accelerate charged particles for material characterization. For example, the technique may be used to accelerate charged molecular ions within a laser-based ion analyzer or mass spectrometer, thereby separating the ions spatially.

A number of embodiments of the invention have been described. Nevertheless, it will be understood that various modifications may be made without departing from the spirit and scope of the invention. Accordingly, other embodiments are within the scope of the following claims.

What is claimed is:

1. A method comprising:
   using a two-dimensional spatiotemporal pulse shaper to produce a spatially and temporally shaped electromagnetic field from an output of a laser system; and
   accelerating a charged particle using at least a transverse electric field component of the spatially and temporally shaped electromagnetic field.

2. The method of claim 1, wherein the transverse electric field component of the shaped electromagnetic field accelerates the charged particle for a period greater than an inverse of an electromagnetic frequency for the shaped electromagnetic field.

3. The method of claim 1, wherein the pulse shaper comprises at least one dispersive element and a two-dimensional modulator.

4. The method of claim 1, wherein the shaped electromagnetic field comprises a series of pulses that follow a trajectory of the accelerated charged particle.

5. The method of claim 1, wherein the charged particle is an electron.

6. The method of claim 1, wherein the accelerated charged particle is directed towards a target to produce a radionuclide.

7. The method of claim 5, further comprising using the accelerated electron as a seed electron in a free electron laser.

8. The method of claim 5, further comprising using the accelerated electron for electron microscopy.

9. The method of claim 5, further comprising using the accelerated electron for electron lithography.

10. The method of claim 1, further comprising inducing electromagnetic emission from the accelerated charged particle.

11. The method of claim 1, wherein the charged particle is a proton.

12. The method of claim 5, wherein the total energy of the accelerated electron is up to 200 MeV.

13. The method of claim 5, wherein the total energy of the accelerated electron is up to 600 MeV.

14. The method of claim 5, wherein the total energy of the accelerated electron is up to 1000 MeV.

15. The method of claim 6, wherein the target comprises a substrate with at least one layer of a proton producing material.

16. The method of claim 1, further comprising using the accelerated charged particle to induce at least one nuclear reaction in a target.

17. The method of claim 1, further comprising using the accelerated charged particle to generate bremsstrahlung radiation in a target.

18. The method of claim 5, further comprising using the accelerated electron for electron diffraction.

19. An apparatus comprising:
a source of charged particles; and
a source comprising a laser and a two-dimensional pulse shaper for providing a temporally and spatially shaped electromagnetic field configured to accelerate at least one of the charged particles using at least a transverse electric field component of the spatially and temporally shaped electromagnetic field.

20. The apparatus of claim 19, wherein the transverse electric field component of the shaped electromagnetic field accelerates the charged particle for a period greater than an inverse of an electromagnetic frequency for the shaped electromagnetic field.

21. The apparatus of claim 19, wherein the two-dimensional pulse shaper comprises at least one dispersive element and a two-dimensional modulator.

22. The apparatus of claim 19, wherein the shaped electromagnetic field comprises a series of pulses that follow a trajectory of the accelerated charged particle.

23. The apparatus of claim 19, further comprising a chamber comprising a target to which the accelerated charged particles are directed.

24. The apparatus of claim 23, wherein the target produces radionuclides in response to the accelerated charged particles.

25. The apparatus of claim 23, wherein the target undergoes a nuclear reaction in response to the accelerated charged particles.

26. The apparatus of claim 23, wherein the target generates bremsstrahlung radiation in response to the accelerated charged particles.

27. An apparatus comprising:
a source of charged particles;
a means for accelerating at least one of the charged particles using at least a transverse electric field component of a spatially and temporally shaped electromagnetic field; and
a target for the accelerated charged particle,
wherein the means for accelerating at least one of the charged particles comprises a two-dimensional spatiotemporal pulse shaping means configured to produce the spatially and temporally shaped electromagnetic field from an output of a laser system.

28. The method of claim 1, wherein the shaped electromagnetic field comprises a plurality of components that follow a trajectory of the accelerated charged particle.

29. The apparatus of claim 19, wherein the shaped electromagnetic field comprises a plurality of components that follow a trajectory of the accelerated charged particle.

* * * * *

UNITED STATES PATENT AND TRADEMARK OFFICE
CERTIFICATE OF CORRECTION

PATENT NO. : 7,348,569 B2  Page 1 of 1
APPLICATION NO. : 11/155011
DATED : March 25, 2008
INVENTOR(S) : Thomas Feurer, Darius H. Torchinsky and Keith A. Nelson It is certified that error appears in the above-identified patent and that said Letters Patent is hereby corrected as shown below:

Cover Page
Second column, References Cited, Other Publications, Entry 2, Ewald, et al., delete "Relativistc" and insert --Relativistic--
Second column, References Cited, Other Publications, Entry 6, Liesfeld, et al., delete "Phyics" and insert --Physics--

Signed and Sealed this

Fifth Day of August, 2008

JON W. DUDAS
*Director of the United States Patent and Trademark Office*